| United States Patent [19] | [11] Patent Number: 4,765,972 |
|---|---|
| Safa et al. | [45] Date of Patent: Aug. 23, 1988 |

[54] VINCA ALKALOID PHOTOACTIVE ANALOGS AND THEIR USES

[75] Inventors: Ahmad R. Safa, Laurel; Ronald L. Felsted, Phoenix, both of Md.

[73] Assignee: The United States of America as represented by the Department of Health and Human Services, Washington, D.C.

[21] Appl. No.: 847,714

[22] Filed: Apr. 3, 1986

[51] Int. Cl.$^4$ ............... A61K 43/00; C07D 519/04
[52] U.S. Cl. ................................ 424/1.1; 435/35; 540/478
[58] Field of Search ............ 540/478; 514/283; 424/1.1

[56] References Cited

U.S. PATENT DOCUMENTS 4,203,898  5/1980  Cullinan et al. .................... 540/478

OTHER PUBLICATIONS

Rahmani, et al., Chemical Abstracts, vol. 98, 191917 8v, (1983).
Cornwell, et al., Chemical Abstracts, vol. 105, 108022j, (1986), abstract of Proc. Natl. Acad. Sci. U.S.A., 1986, 83(11), pp. 3847–3850.
Safa, et al., J. Biological Chemistry, vol. 261, No. 14, pp. 6137–6140, (05/15/86).
Cornwell, et al., Proc. Natl. Acad. Sci. U.S.A., vol. 83, pp. 3847–3850, (06/86).
Safa, et al., Biochemistry, vol. 26, No. 1, pp. 97–102, (01/13/87).
Safa, et al., J. Biological Chemistry, vol. 262, No. 3, pp. 1261–1267, (01/25/87).

*Primary Examiner*—Nicholas S. Rizzo
*Assistant Examiner*—Diana G. Rivers
*Attorney, Agent, or Firm*—Browdy & Neimark

[57] ABSTRACT

Pharmacologically active, radioactive, and photoactive vinblastine analogs are provided which can be used to bind covalently to cellular polypeptides which have high affinity for Vinca alkaloids. The compounds are N-(p-azido[3,4-$^3$H]benzoyl)-N'beta-aminoethylvindesine and N-p-azido-[3-$^{125}$I]-salicyl-N'-beta-aminoethylvindesine. The compounds can be used to identify cellular Vinca alkaloid receptors which may be involved in antineoplastic, cytotoxic and drug resistant mechanisms of actions. In addition to specific interaction with tubulin, these compounds specifically bind to a 150–180 kDa surface membrane glycoprotein which is overexpressed in multidrug resistant cells.

5 Claims, 17 Drawing Sheets

VINBLASTINE

N-(p-AZIDO-3,5-[$^3$H] BENZOYL)-N'-β-AMINOETHYL VINDESINE

N (p-AZIDO-3-[$^{125}$I] SALICYL)-N'-β-AMINOETHYLVINDESINE

VINCA ALKALOID PHOTOACTIVE ANALOGS AND THEIR USES

FIELD OF THE INVENTION

The present invention relates to analogs of Vinca alkaloids which can be used to identify and characterize Vinca alkaloid binding polypeptides in normal and cancerous tissue and cells, as well as to establish relationship between interactions and antimitotic, antineoplastic, and drug resistance mechanisms.

BACKGROUND OF THE INVENTION

The Vinca Alakloids, including vinvblastine and vincristine, isolated from the plant *Vinca rosea* L., are important chemotherapeutic agents which have been found to have clinical activity against a spectrum of human cancers. It is generally assumed that the mechanism for their cytotoxic, anitmitotic, and antineoplastic activity is related to their binding to the tubulin dimer of microtubules, with the subsequent depolymerization and disruption of the cellular microtubular network including the mitotic spindle. However, evidence from several studies now suggests that binding to mitotic spindle tubulin dimers cannot account for their pronounced cytotoxic effects on slow proliferating, sensitive cells and interphase cells, since in these cells cytotoxicity is evident long before mitotic arrest is manifest.

Tubulin also exists as a plasma membrane component in brain and thyroid tissues, and in vinblastine-sensitive human lymphoblasts with leukemic origin. The possibility that these drugs may exert their cytotoxic effects by interacting with the membrane tubulin component rather than cytoplasmic microtubules suggests that the mechanism for cytotoxic and cytostatic effects of these alkaloids may be more complex than simple depolymerization and disruption of mitotic spindles.

For example, Vinca alkaloids have been shown to inhibit the incorporation of $^3$H-uridine into RNA and $^3$H-thymidine in DNA. These effects may be due to the specific inhibition of nucleic acid synthesis as well as inhibition of nucleotide uptake into the cells. Similarly, vinblastine can precipitate a number of acidic proteins and nucleic acids in addition to tubulin.

Unfortunately, our knowledge of the mechanism involved in expression of Vinca alkaloid resistance in cancer cells is limited. While oversynthesis of particular proteins in Vinca alkaloid resistance cells has been noted, no attempt has been made to discover relationships between such proteins and their possible interactions with these drugs.

Previous studies of drug-protein interactions required purified protein components for equilibrium binding measurements under optimum conditions. Accordingly, these studies were costly and difficult to perform.

Affinity labelling of proteins with photoactive ligands is a powerful tool for probing biochemical targets. In particular, photoaffinity labelling has been used for identification, purification, and characterization of mediators of biological, physiological, and pharmacological activities. The photoaffinity labelling technique allows for investigation of drug-protein interactions in order to identify an acceptor molecule in a mixture of candidates or to identify a specific component of a multi-subunit system. During photoaffinity, a reversible complex presumably forms between the photoactive analog and unique acceptor sites of specific polypeptides which preferentially recognize the characteristic structure of the drug. Upon irradiation with UV light, the analog is converted into a highly reactive nitrene intermediate which will covalently interact with the acceptor sites. A particular functional group at the acceptor site need not be present because the photogenated species can react even with carbon-hydrogen bonds.

The exposure of malignant cell lines to natural product cytotoxic drugs such as vinblastine, actinomycin D, adriamycin, or colchicine, frequently results in the isolation of populations of cells with resistance to the selecting agent as well as a collateral resistance to other mechanistically distinct and structurally unrelated compounds. The mechanisms by which these cell lines become multidrug-resistant is unknown, but it is thought to be related to a parallel reduction in the cellular accumulation of those drugs to which the cells are resistant. The multidrug-resistant phenotype also is characterized by the presence of a 150-180 kDa surface membrane glycoprotein (gp150-180) which occurs in multidrug-resistant cells in direct proportion to the degree of their acquired drug-resistance. The relationship of gp150-180 to multidrug resistance is not known. It may accumulate only as a secondary consequence of the multidrug-resistant phenotype. Alternatively, gp150-180 could promote multidrug-resistance by direct or indirect effects on membrane permeability drug transport, or drug binding.

SUMMARY OF THE INVENTION

It is an object of the present invention to provide pharmacologically active, radioactive, photoactive, vinblastine analogs.

It is a further object of the present invention to provide methods of determining the biochemical mechanisms of Vinca alkaloid action.

The pharmacologically active, radioactive, photoactive Vinca alkaloid analogs of the present invention are capable of covalently binding to unique cellular polypeptides which have high affinity for parent Vinca alkaloids. The compounds of the present invention are valuable in identifying cellular receptors which may be involved in novel as well as in known mechanisms of Vinca alkaloid actions. Knowing the properties of the parent drug, plus the ability to photoactivate the analog, the analog can easily probe specific receptors for the parent drugs in the cells, making these analogs useful tools for research purposes. Without such analogs which are photoactive or radioactive, it is impossible to probe interactions of Vinca alkaloids with their receptors in cells and in tissue homogenates. The two compounds of the present invention are photoactive analogs of vinblastine.

The first compound, N-(p-azido-[3,4-$^3$H]benzoyl)-N'-beta-aminoethylvindesine ($^3$H-NABV) has the same affinity as vinblastine for tubulin, and exhibits nearly identical biochemical and pharmacological properties as the parent compound. As a close vinblastine homolog, this photoactive probe has been found to be an excellent probe for identifying cellular vinblastine acceptors which might have functional significance in multidrug-resistant cells.

The second compound, N'-(p-azidosalicyl)N'-beta-aminoethylvindesine, can be used as well as the first compound to photoaffinity label a 150-180 kDa component in multidrug-resistant Chinese hamster lung DC-3F cells. This radiolabelled component was identified by immunoprecipitation as the same gp150–180 which is present in high amounts in multidrug-resistant cell ines. The identification of gp150–180 as a specific vinblastine acceptor is a first step in defining its possible role in the multidrug-resistance phenomenon.

DETAILED DESCRIPTION OF THE INVENTION

Example I

N-(p-azidobenzoyl)-N'-beta-aminoethylvindesine, also known as NABAV or NABV, was prepared from N-beta-aminoethylvindesine and N-hydroxy-succinimidyl-4-azidobenzoate (NAB). Five micromoles of N-beta-aminoethylvindesine were dissolved in 1 ml of chloroform. To this were added 10 micromoles of N-hydroxy-succinimidyl-4-azidobenzoate (Pierce Chemical Co., Rockford, Ill.). The reaction mixture was maintained at 4° C. overnight. Progress of the reaction was monitored by silica gel GHLF scored plates. To purify the product, the reaction mixture was applied to a column (0.5×8 cm) of silica gel which was preeluted with NAB and washed extensively with chloroform. The product was eluted from the column with 5% methanol and 95% chloroform. A yield of 52% was obtained.

The product was further purified with high pressure liquid chromatography on a micro Bondapak C-18 column (3.9 mm×30 cm) (Waters Associates, Milford MA). The system consisted of two pumps (Model 100A, Beckman Instrument Co.) and an absorbance detector (Model 160, Beckman Instrument Co.) set at 254 nm with a sensitivity of 0.1 absorbance unit full scale. The system was equipped with a data processor chromatopac (Altex C-RlA, Schimadyer Corporation, Kyoto, Japan). The reversed phase method of a 30 min, gradient of 60–90% methanol in $dH_2O$ containing 0.19% diethylamine (Aldrich Chemical Co., Milwaukee, WI) at a flow rate of 1.5 ml/min., with an additional 10 minues isocratic 90% methanol, 0.19% diethylamine at the end of the gradient, was used. Samples of 20 microliters in methanol were injected into the column. With this system, vinblastine (VB) and NABV have retention times of 9.43 and 16.48 minutes, respectively. Purification of NABV was carried out in the absence of UV monitoring. The product was collected and the methanol was evaporated with a stream of nitrogen gas, and the remaining solution was extracted with chloroform and evaporated. The reversed phase HPLC indicated a single peak of the product identical to 99% of the absorbance, as shown in FIG. 1. The product gave a single UV absorbing spot on silica gel TLC with fluorescent indicator (E. Merck, Darnstadt, Germany, Solvent I: chloroform:methanol:$H_2O$; 80:20:2), with a R =0.72 compared to VB $R_f$=0.81. The product exhibited an IR spectrum with a strong azide response at 2120 $cm^{-1}$. The molecular weight of the product was 941 compared to that of 810 for VB as revealed by FAB mass spectrometry.

N-(p-azido-3,5-($^3H$)-benzoyl)-N'-aminoethylvindesine

One to 1.38 mole of N-hydroxysuccinimidyl-4-azido-3,5-($^3H$)-benzoate (50.6 Ci/mmol) in 0.05 ml isopropanol (New England Nuclear, Boston MA) was added to 0.45 ml (0.5–0.7 micromol) solution of B-beta-aminoethylvindesine in chloroform, and the mixture was maintained at 4° C. for 48–72 hours. The product was purified by silica gel column and reversed phase HPLC, respectively, as described for the non-radioactive compound, above. The identity and purity of the compound were confirmed by co-chromatography with NABV by TLC in solvent and HPLC.

Example II

N-(p-azidosalicilyl)-N'-beta-aminoethylvindesine (NASAV)

The synthetic procedure for NASAV was similar to that of NABV. Five micromoles of N-beta-aminoethylvindesine was dissolved in 1 ml of chloroform. To this was added 10 micromole of N-hydroxysucciminidyl-4-azidosalicylic acid (Pierce Chemical Co., Rockford, Ill.). The reaction mixture was applied to a preparative taper plate in silica gel with fluorescent indicator (analtech, Newark, DE.), which was predeveloped in Solvent II (chloroform: methanol: 40% aqueous methylamine; 80:20:4) overnight. Following thin layer chromatography in Solvent II, the product was purified by scraping silica gel from the plate, extracting it with chloroform, and recovering the product with evaporation with a stream of nitrogen.

The product gave a single UV absorbing spot on silica gel thin layer chromatography with fluorescent indicator (E. Merck). (Solvent II, $R_f$=0.73). The product exhibited a UV-visible absorption spectrum which consisted of a composite of the absorption spectra of vinblastine and the azidosalicylate chromophore. Upon UV irradiation, the absorption between 250–300 nm was lost, yielding a spectrum nearly identical to vinblastine. Fast atom bombardment mass spectroscopy yielded a MH+=958. The final product exhibited an IR spectrum with a strong azide response at 2120 $cm^{-1}$.

N-(p-azido-3-[$^{125}I$-]-salicyl-N'-beta-aminoethylvindesine; [$^{125}I$]-NASV

This compound was synthesized in two step reactions. In the first step, 1.67 nanomoles of N-hydroxysuccinimidyl-4-azidosalicylate (NAS, Pierce Chemical Co., Rockford, IL), were dissolved in 15 microliters of acetonitrile. Five micromoles of 0.5M sodium phosphate, pH7, and 5 mCi Na $^{125}I$ in 10 microliters of 0.1 1N NaOH was added. Then 2.5 nmoles of chloroamine T in 10 microliters of a mixture of acetonitrile and dimethylformamide (1:1) were added, and the mixture was kept for two minutes at room temperature. Three hundred microliters of 10% NaCl were added, and the reaction mixture was extracted with 300 microliters of ethyl acetate. The extract was evaporated under nitrogen, and the reaction mixture was chromatographed on a silica gel G thin layer using benzene, chloroform, ethyl acetate, and acetic acid (1:1:1:0.1, v/v). As revealed by autoradiography, the product N-hydroxysuccinimidyl-3-[$_{125}I$]-4-azidosalicylate) gave a radioactive spot accounting for 90% of radioactivity ($R_f$=0.4).

The product was dissolved in 0.45 ml chloroform, and 0.5. mole N-beta-aminoethylvindesine was added. The mixture was kept at 4° C. for 48–72 hours. The [$_{125}I$]-NASV was purified by reversed phase HPLC as described above for purification of NASV. In this system, [$_{125}I$]-NASV had a retention time of 22.6 minutes.

The product gave a single radioactive spot on silica gel thin layer chromatography with a $R_f$=0.66 for solvent I and $R_f$=0.78 for solvent II as revealed by autoradiography.

The compounds of this example are particularly useful in the identification of specific Vinca alkaloid binding polypeptides in tissue and tumor cells. The compounds have been used to identify Vinca alkaloid binding polypeptides in calf brain homogenates, in tumor cell lines, and in resistant cell lines. Additionally, the compounds have been found useful in identifying and characterizing Vinca alkaloid specific acceptor sites in calf brain tubulin, and the inherent pharmacological activity and ultrastructural effects in tumor cell lines. The compounds have also been found useful in screening for drug acceptors in Vinca alkaloid or multidrug-resistant cells in human tumor biopsies.

Example III

N-(p-azido-[3,4-$^3$H]benzoyl)-N'-beta-aminoethylvindesine ($^3$H-NABV)

($^3$H-NABV was prepared from N-beta-aminoethylvindesine and N-hydroxysuccinimidyl-4-azido-[3,5-$^3$H]benzoate (50.6 Ci/nmole; New England Nuclear, Boston, MA), as described above. This vinblastine analog is both radioactive and photoactive.

Cell lines were cultured as described by Peterson et al., *Cancer Res.* 43, 222–228 (1983) and by Meyers et al., *J. Cell. Biol.* 100, 588–597 (1985). Vincristine-resistant (DC-3F/VCRd-5L, 2750-fold resistant) and actinomycin D-resistant (DC=3F/ADX, 2450-fold resistant) variants were selected from Chinese hamster lung (DC-3F) cells as described in the above-cited articles. The drug-sensitive revertant (DC-3F/ADX-U, 30-fold resistant to actinomycin D) was obtained from DC-3F/ADX cells grown in the absence of drugs. The resistant cells expressed a typical multidrug-resistant phenotype as typified by cross-resistance to a number of unrelated natural product compounds. Whole cell particulate fractions were prepared by the sonication of drug-sensitive or drug-resistant cells in 50 mM potassium phosphate buffer (pH 7.4), followed by centrifugation at 100,000×g for one hour. The particulate pellet was washed by resuspending in the same buffer, and the whole cell particulate fraction was obtained by a second centrifugation. Purified plasma membranes were prepared by sucrose density gradient centrifugation as described in Peterson et al in *J. Supramolecular Structure* 9, 289–298 (1978). Protein concentrations were determined by the procedure of Lowry et al., *J. Biol. Chem.*, 193, 265–275 (1951).

Immunoprecipitations were performed by extracting membranes (20 micrograms protein) for fifteen minutes at 4° C. with 100 microliters of 50 mM Tris-HCl buffer (pH 7.0) containing 150 mM NaCl, 1% Triton X-100, 1% sodium deoxycholate, 0.1% SDS, 1 mM ethylenediamine tetraacetic acid, 1 mM phenylmethylsulfonyl-fluoride, and 10 mg/ml Trayslol (Boehringer Mannheim, Indianapolis, IN). The mixtures were then incubated for one hour at 5° C. with 10 microliters rabbit polyclonal antibody specific for multidrug-resistant 150–180 kDa surface membrane glycoprotein (gp150-180). Immune complexe were obtained by incubating the mixture with Protein A-Sepharose (Pharmacia, Piscataway, NJ) for one hour at 5° C. and recovering the beads after washing four times. Specific rabbit polyclonal antibody was prepared by immunizing rabbits with three intravenous injections of 5×10$^7$DC-3F/VCRd-5L cells as described by Meyers et al. in *Proc. Natl. Acad. Sci. U.S.A.* In press (1986), except that the antiserum was not preabsorbed with DC-3F cells. Nonimmune rabbit serum was used as a control.

Photolabelling of membrane samples (50 micrograms protein) was performed in 40 nM potassium phosphate buffer (pH 7.0) containing 4% Me$_2$SO and 50 nM of either $^3$H-NABV (0.1 microCi) or $^{125}$I-NASV (0.2 microCi) in a final volume of 0.050 ml. After preincubation in the presence or absence of vinblastine, irradiation was performed using a UV lamp (302 nm or 366 nm, respectively) for 20 minutes at 25° C. SDS-PAGE of 5–15% gradient gels containing 4.5 M urea, fluorography, and autoradiography were performed as described by Felsted et al. in *Blood* 66, 606–613 (1985). The quantitation of radiolabelling was accomplished by cutting appropriate areas from the gel and counting the pieces in a gamma counter.

Whole cell particulate fractions from Chinese hamster lung drug-sensitive (DC-3F) cells and from a multi-drug-resistant (DC-3F/VCRd-5L) variant originally selected for resistance to vincristine were photolabelled with $^3$H-NABV and analyzed by SDS-PAGE. Fluorography revealed a prominent high molecular weight, radiolabelled doubles (150–180 kDa) in drug-resistant cells but not in drug-sensitive cells, as shown in FIG. 8. This radiolabelled doublet consisted of a high molecular weight major band and a smaller minor band. The proportions of the two radiolabelled bands in the doublet varied with each whole cell particulate or purified membrane preparation and it was felt that this variation may result from the partial proteolysis of the larger radiolabelled species. A similar phenomenon has been reported for the epidermal growth factor receptor, by Cassel et al. in *J. Biol. Chem.* 257, 9845–9848 (1982). A number of other minor radiolabelled species which were common to both cell lines also were observed. Photolabelling specificity was determined by performing the experiments in the presence of 10 micromoles vinblastine. Under these conditions, radiolabelling of the 150–180 kDa component was substantially reduced, while the radiolabelling of other common species was not affected. Finding a specific vinblastine binding 150–180 kDa component in drug-resistant cells but not in drug-sensitive cells suggests that there may be a direct functional role for this Vinca alkaloid specific acceptor in the vincristine resistance mechanism. The fact that similar 150–180 membrane glycoproteins are found in many different multidrug-resistant cell lines suggests that this radiolabelled acceptor may play a role in the development of multi-drug resistance as well.

A plasma membrane localization for the 150–180 kDa component was established by photoaffinity labelling sucrose density gradient purified plasma membranes from drug-sensitive and drug-resistant cells with $^3$H-NABV. The results were similar to those obtained with the crude particulate fractions except that radiolabelling of the 150–180 kDa component was increased relative to background labelling and radiolabelling in the presence of 10 micromole vinblastine was reduced by 59%. These membranes, as well as membranes from another multidrug-resistant variant (DC-3F/ADX) originally selected for resistance to actinomycin D and from a revertant (DC-3F/ADX-U) obtained from the DC-3F/ADX variant were also photoaffinity labelled with $^{125}$I-NASV. In the case of $^{125}$I-NASV, autoradiographs revealed that the 150–180 kDa component was very faintly radiolabelled in the drug-sensitive parental cells, but that radiolabelling in the drug-resistant variants was increased up to 150-fold. In contrast, radiolabelling of the 150–180 kDa component in the DC-3F/ADX-U revertant cells was increased by only about 15-fold. In the presence of 10 micromoles vinblastine, the radiolabelling of the 150–180 kDa component was reduced 80–90% in the drug-resistant variants and was completely absent in the parental and revertant cells. In other studies, a number of drug-sensitive cell lines have been shown by immunoblottings to have barely detectable levels of analogous 150–180 kDa surface membrane glycoproteins compared to the corresponding multidrug-resistant variants. Those observations are consistent with the proposal that increases in the 150–180 kDa membrane glycoproteins result from the amplification of a normally expressed gene product.

The vinblastine photoaffinity labelled 150–180 kDa component was found to comigrate on SDS-PAGE exactly with a Coomassie blue stained polypeptide seen only in drug-resistant variants. Membranes from parental cells and from the DC-3F/VCRd-5L drug-resistant variant were photolabelled with $^{125}$I-NASV, detergent solubilized and immunoprecipitated with a polyclonal antibody which has been shown to cross react with the gp150–180 from several multidrug-resistant cell lines. The radiolabelled 150–180 kDa polypeptide was immunoprecipitated only from membrane extracts of drug-resistant cells. No radioactivity was precipitated when nonimmune serum was used in place of the specific antibody. As expected, when photolabelling was performed in the presence of 10 microliters of vinblastine, the radiolabel in the immunoprecipitae was reduced 96%. These results demonstrate that the vinblastine photoaffinity labelled 150–180 kDa polypeptide is immunocross-reactive with the gp150–180 present in a number of different multidrug-resistant cell lines. This drug acceptor may also be identical to a similar high molecular weight polypeptide identified in a wide variety of cell lines by antibodies specific to the P-glycoprotein.

Tissue Homogenate High Speed Supernatant and Pellet Fractions

Tissue homogenate high speed supernatant and pellet fractions were obtained by homogenizing 1 gram of calf brain in 10 ml volumes of 0.05 M potassium phosphate buffer, pH 7.4, for one minute with a Model PCU Polytron homogenizer with a PT-10-ST probe operated at 50% maximum power (Brinkmann Instruments, Westbury, NY). The brain tissue homogenate was collected after filtering through one layer of cheesecloth. Brain tissue high speed supernatant fractions were prepared by centrifuging the homogenates at 100,000×g for 60 minutes at 4° C. The resulting pellet was washed twice with five times its original volume of buffer, and recentrifuged as described. Protein concentrations and supernatant fractions were stored in small aliquots in liquid nitrogen and thawed only once.

Photolabelling with 3H-NABV

The standard photolabelling mixture used contained 50 nM $^3$H-NABV (50.6 Ci/mmol), 4% dimethylsulfoxide, 40 nm potassium phosphate buffer, pH 7.0, and 2 mg/ml of tissue homogenate or high speed pellet or supernatant fractions in a final volume of 0.05 ml in polyvinylchloride V-microtiter wells (Dynatech Labs, Inc., Alexandria, VA) in a 25° C. water bath. Photolabelling mixtures were incubated for 15 minutes at 25° C. before photolysis. Photoactivation was performed for 10–20 minutes with a UV light equipped with two 15 W self-filtering 302 nm lamps (Model xx-15, Ultra-Violet Products, Inc., San Gabriel, CA), placed 3.4 cm above the photolabelling mixture. Complete photolysis of 3H-NABV (15 minuets of UV light) in the presence of either a high concentration (>20 microM) of vinblastine or 0.5 mM of the nitrene scavenger, p-aminobenzoic acid, was demonstrated by thin layer chromatography of the chloroform extracted photoactivated reaction mixture in the absence of protein. In a control experiment, brain homogenate was irradiated in the presence of 50 nM $^3$H-vinblastine (10.7 Ci/mmol; Amersham Corp., Arlington Heights, IL). Photoactivated samples were immediately processed for SDS-PAGE or frozen at −70° C.

Characterization of Macromolecular Composition of Vinca-Alkaloid Binding Components After photolabelling calf brain homogenates (100 mg) with $^3$H-NABV, the homogenates were treated with 1 mg/ml proteinase K (Bethesda Research Laboratories, Gaithersburg, MD) in 2% SDS, 2.5 mM EDTA and 50 mM glycine-NaOH buffer, pH 10.1 (final volume, 0.1 ml) for 60 minutes at 37° C. Alternatively, the calf brain homogenates was treated with 0.214 mg/ml DNase (2182 units/mg; Millipore, Bedford, MA), or 6.9 mg/ml RNase (3220 units/mg, Milliore) in 4.5 mM $MgCl_2$, 18 mM $CaCl_2$ and 2 mM potassium phosphate buffer, pH 7.0 (final volume, 0.1 ml), for 5 minutes at 37° C. Other samples were extracted three times with chloroform: methanol (2:1; v/v) after photolabelling. Also, brain homogenates were heated in a boiling water bath for 20 minutes before photolabelling. These specimens were subjected to SDS-PAGE.

Immunoprecipitation of Photolabelled Tubulin

Immunoprecipitations were performed essentially according to the method of Kessler as described in *J. Immunol.* 115, 1617–1624 (1975). Aliquots of calf brain high speed supernatant or pellet fractions (100 microliters, 160 micrograms protein) were photolabelled with $^3$H-NABV as described above. The photolabelled pellet fractions (100 microliters) were extracted for 15 minutes at 4° C. with 100 microliters of a buffer containing 0.04 M Tris-hydrochloride (pH 7.4), 0.01 M MgCl2, 0.20 M NaCl, 2% Triton X-100 (v/v), 1% sodium deoxycholate, and 6 mM phenylmethylsulfonyl fluoride. Samples were incubated with monoclonal anti-alpha or -beta tubulin (IgG, kappa, light chain; Amersham Corp., Arlington Heights, IL) or non-immune sera at 4° C. To each samples was added 100 microliters of 10% suspension of formalin-fixed *Staphylococcus aureus* (PANSORBIN) (Calbiochem, L Jolla, CA) in phosphate buffered saline (PBS) containing 0.5% NP 40, 0.02% sodium azide and 1 mg/ml ovalbumin (Sigma Chemical Co., St. Louis, MO) After 45 minutes, the bacteria were recovered by centrifugation at 13,000×g in a microcentrifuge and washed three times with 1.5 ml of the PBS buffer (without ovalbumin). Bound tubulin was then solubilized by resuspension of the bacteria in 50 microliters of SDS sample buffer (4% SDS, 8M urea, 0.1 M dithiothreitol, 20% glycerol, 0.04% bromophenol blue, and 0.08 M Tris-HCl buffer, pH 6.8), incubated at 100° C. for five minutes, centrifuged at 13,000×g, and the supernatant fraction analyzed by SDS-PAGE as described below. No label was precipitated when nonimmune serum, PANSORBIN or buffer was used alone.

In-vitro NABV Metabolism Calf brain homogenates (100 micrograms protein) were incubated with 3H-NABV under standard photolabelling conditions for 30 minutes at 25° C. in the absence of UV light. The mixture was then extracted with 1 ml chloroform and analyzed for radioactive materials in the organic extract by silica gel thin layer chromatography using Solvent I.

SDS-Polyacrylamide Gel Electrophoresis

Equal volumes of SDS sample buffer were added to photolabelled mixtures in microliter wells. The mixtures were transferred to 0.5 ml centrifuge tubes. After heating for five minutes at 100° C. on a heating block, the mixtures were cooled on ice and sonicated for five seconds, cooled, and 0.08 ml aliquots of the mixtures were applied to separate wells of a 1.5 mm thick polyacrylamide slab gel.

Electrophoresis was performed as described by Laemmli in Nature (Lond.) 227, 680–685 (1970) with a linear polyacrylamide gradient from 9.7% acrylamide, 0.26% bis-acrylamide and 10% glycerol, to 16.6% acrylamide, 0.44% bis-acrylamide, and 17% glycerol using a Bio-Rad slab gel apparatus (Model 220, Richmond, CA) at 8 mA/gel for sixteen hours. Following fixation and staining of the gel, in 0.25% Coomassie brilliant blue, 45% methanol and 10% acetic acid, the lanes of stained polypeptide corresponding to each sample slot were cut and sliced into 1.0 mm slices. Each slice was incubated with 0.3 ml 30% $H_2O_2$ in a closed scintillation vial at 100° C. for one hour to solubilize the gel slice, with radioactivity subsequently quantitated. The molecular weights of radioactive macromolecules were estimated by their mobilities relative to standard proteins of known molecular weights. (Bio-Rad, Richmone, CA). The radioactivity of photolabelled components was quantitated in triplicate by adding the dpm in each 1 mm gel slice through the radioactive peak. The average baseline radioactivity was subtracted from each value and the results were presented as means ± standard deviation.

Gel electrophoresis densitometry was performed on a Beckman DU-8 UV-visbile computing spectrophotometer measuring absorbance at 500 nm. Areas under all peaks were computed as compared to the absorbance at the lowest valley throughout the gel line.

Characterization of
N-(p-azidobenzoyl)-N'-beta-aminoethylvindesine

The photoactive Vinca alklaoid analog, NABV, was prepared as described in Example I. The analog was purified by HPLC. Values of the absorption peaks measured by IR, the response frequencies measured by HNMR and the FAB mass spectral analysis confirmed the structure of NABV. The UV-VIS absorption spectra of the product showed a close composite of the absorption spectra of its p-azidobenzoyl chromophore ( max=269 nm), and the absorption spectra of vinblastine between 280–340 nm. Irradiation with UV light caused a time-dependent loss in 250–300 nm absorption of NABV yielding a final spectrum very similar to vinbalstine. The UV-spectrum of the parent compound, vinblastine, was not affected by UV light.

The above-described examples provide the first evidence that gp150–180 can serve as a specific cellular acceptor in vitro for one of the drugs invariably associated with the multidrug-resistant phenotype. The photolabelling of gp150–180 in intact cells can be used to establish whether this membrane glycoprotein also functions as a drug-acceptor in vivo.

DETAILED DESCRIPTION OF THE DRAWINGS

Figure 1:
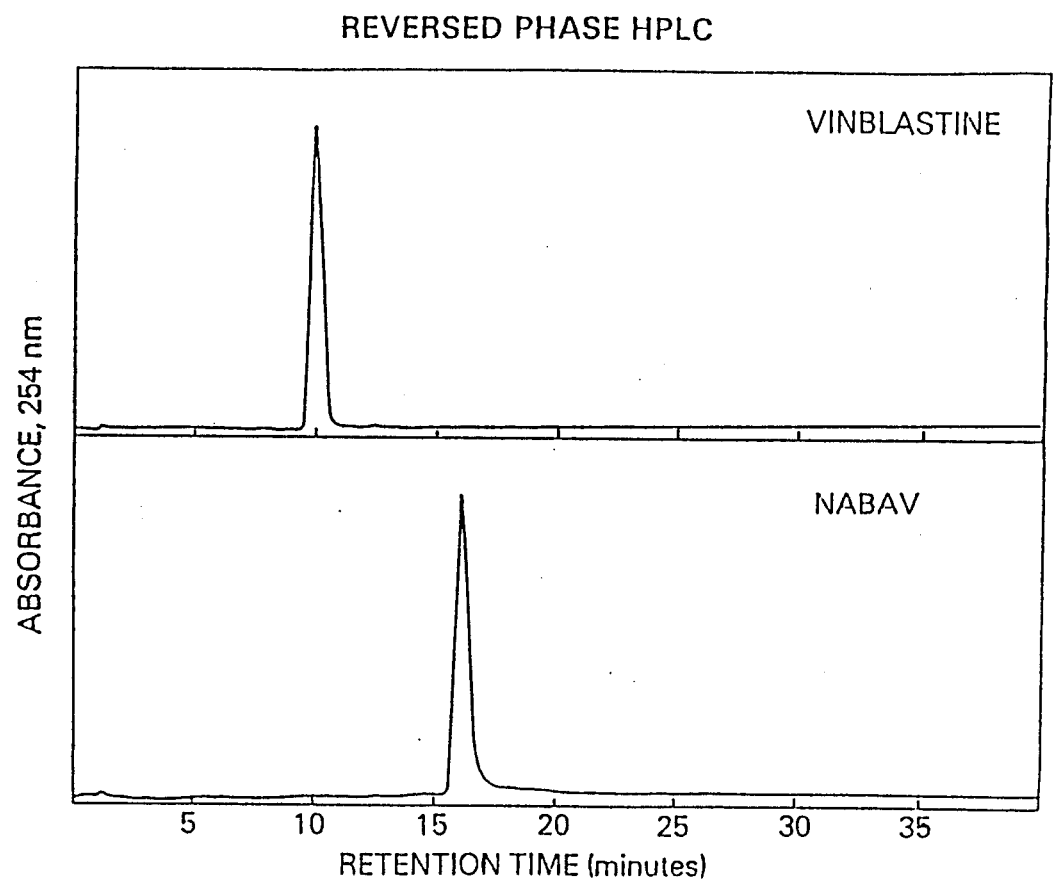
FIG. 1 shows the reverse-phase HPLC chromatograph of vinblastine and NABAV. A 30-minute gradient of 60–90% methanol, 0.19% diethylamine followed by isocratic 90% methanol, 0.19% diethylamine at a flow rate of 1.5 ml/minute was used.
Figure 2:
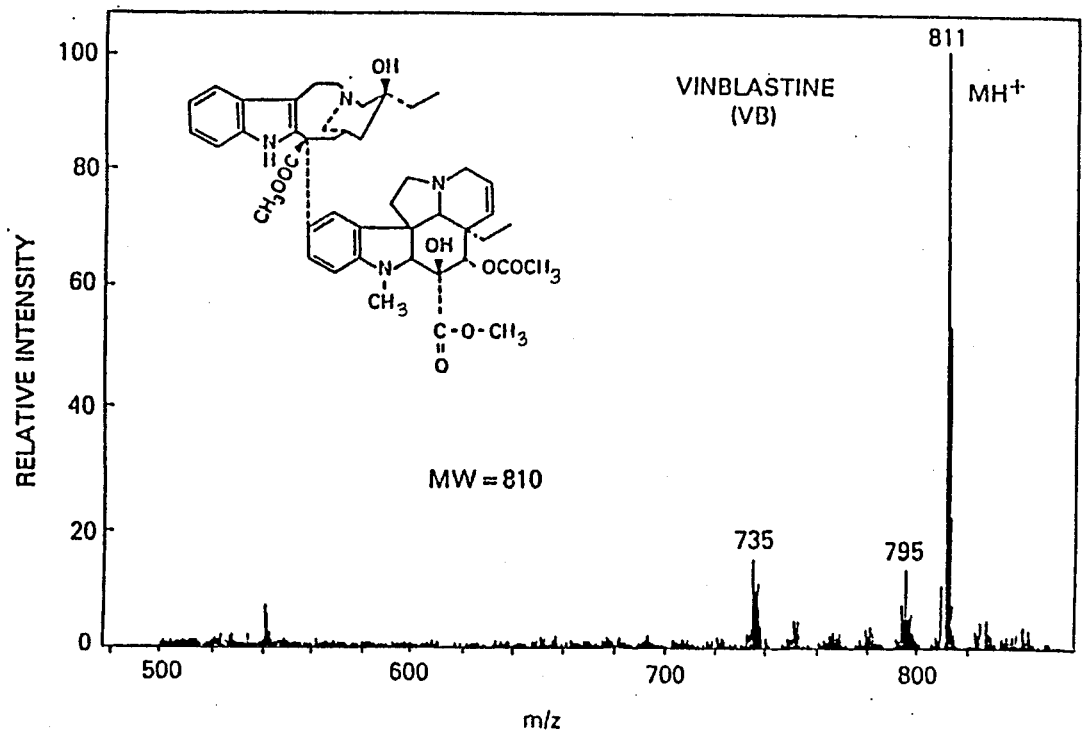
FIG. 2 shows the FAB mass spectrum and structural formula of vinblastine.
Figure 3:
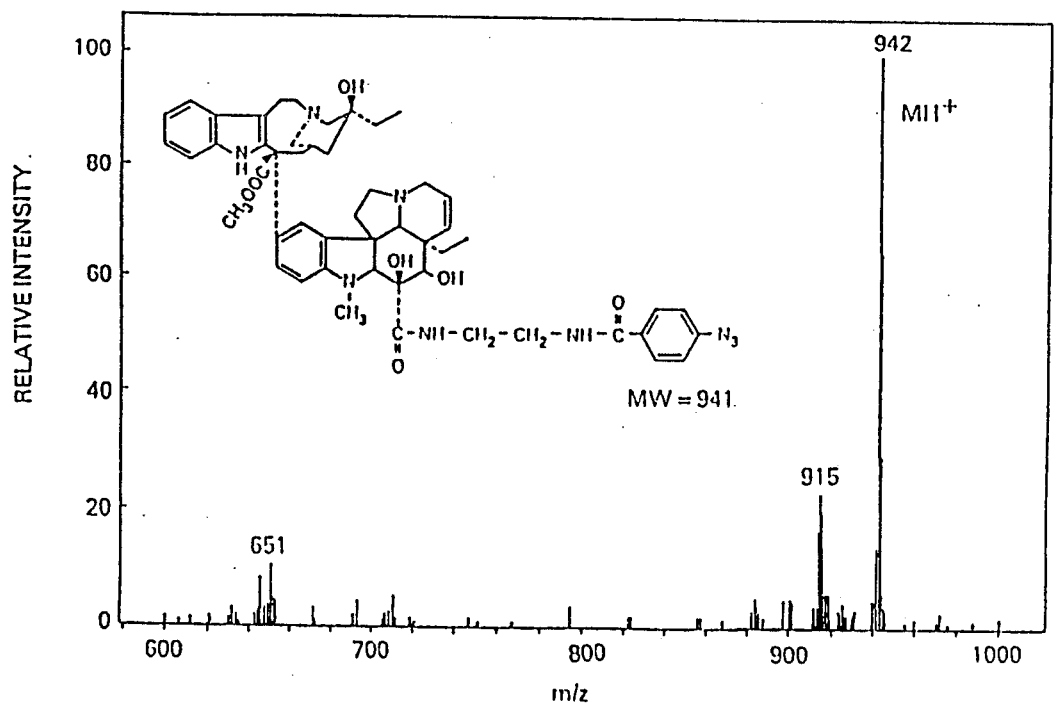
FIG. 3 shows the FAB mass spectrum and structural formula of NABAV.
Figure 4:
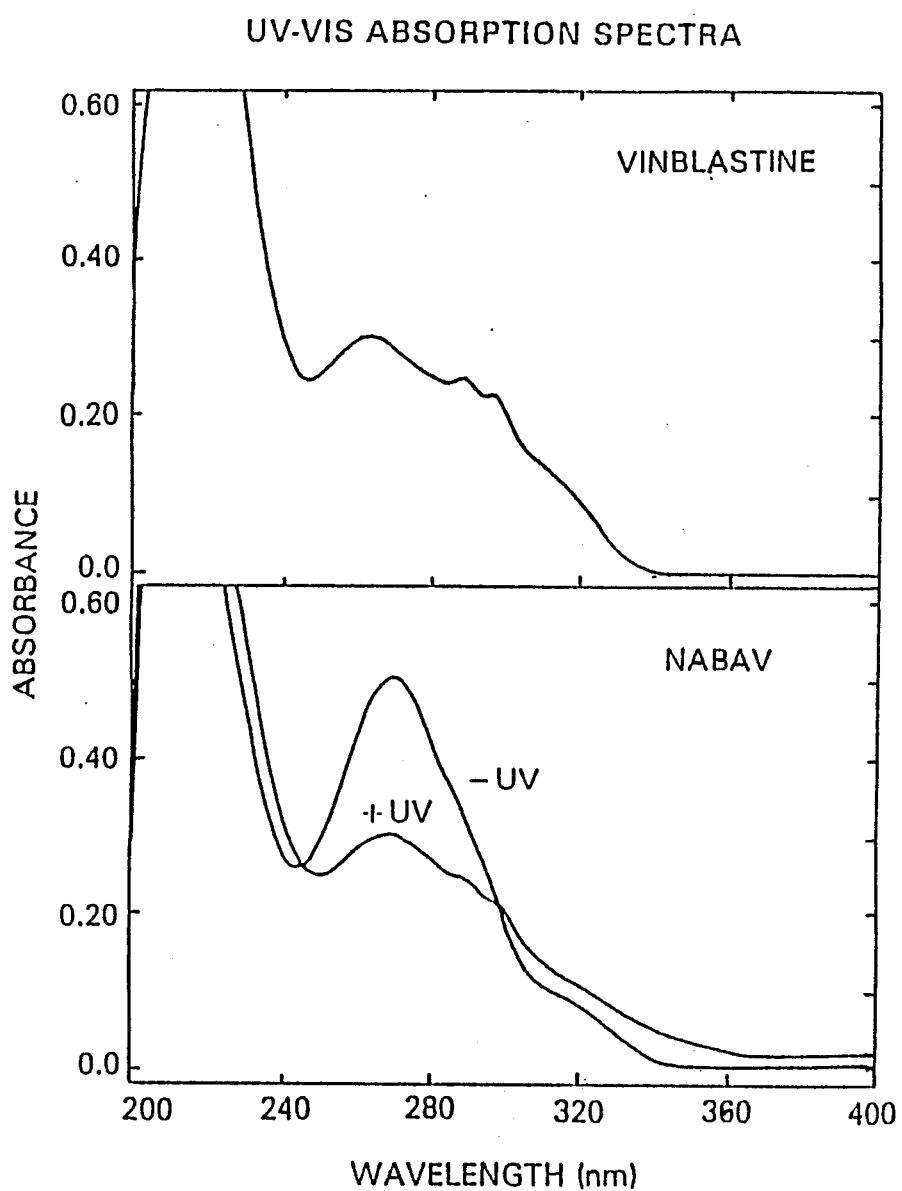
FIG. 4 shows the UV-VIS absorption spectra for vinblastine, NABAV, (−UV) and NABAV after irradiation at 302 nm for five minutes (+UV).
Figure 5:
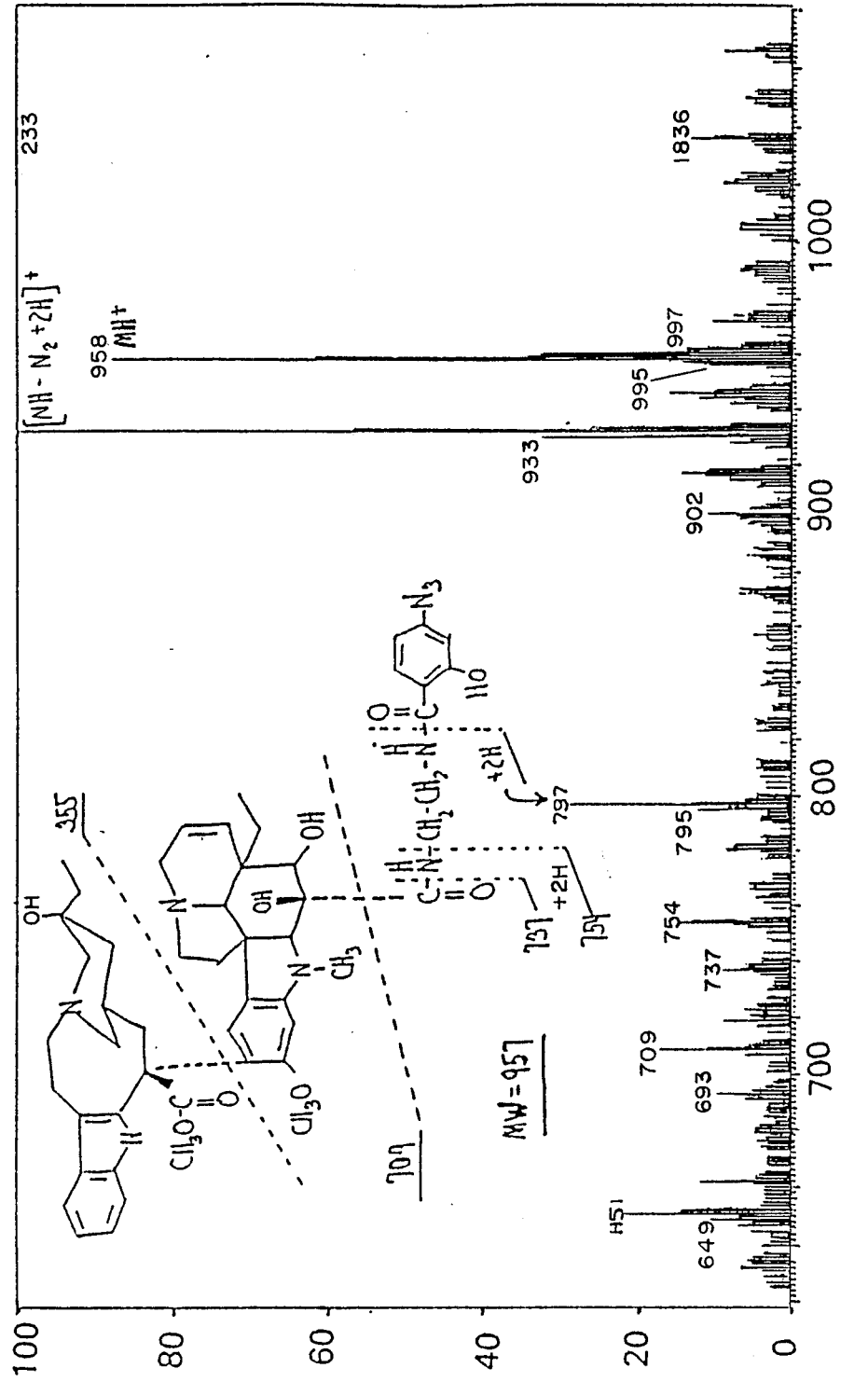
FIG. 5 shows the FAB mass spectrum of NASAV.
Figure 6:
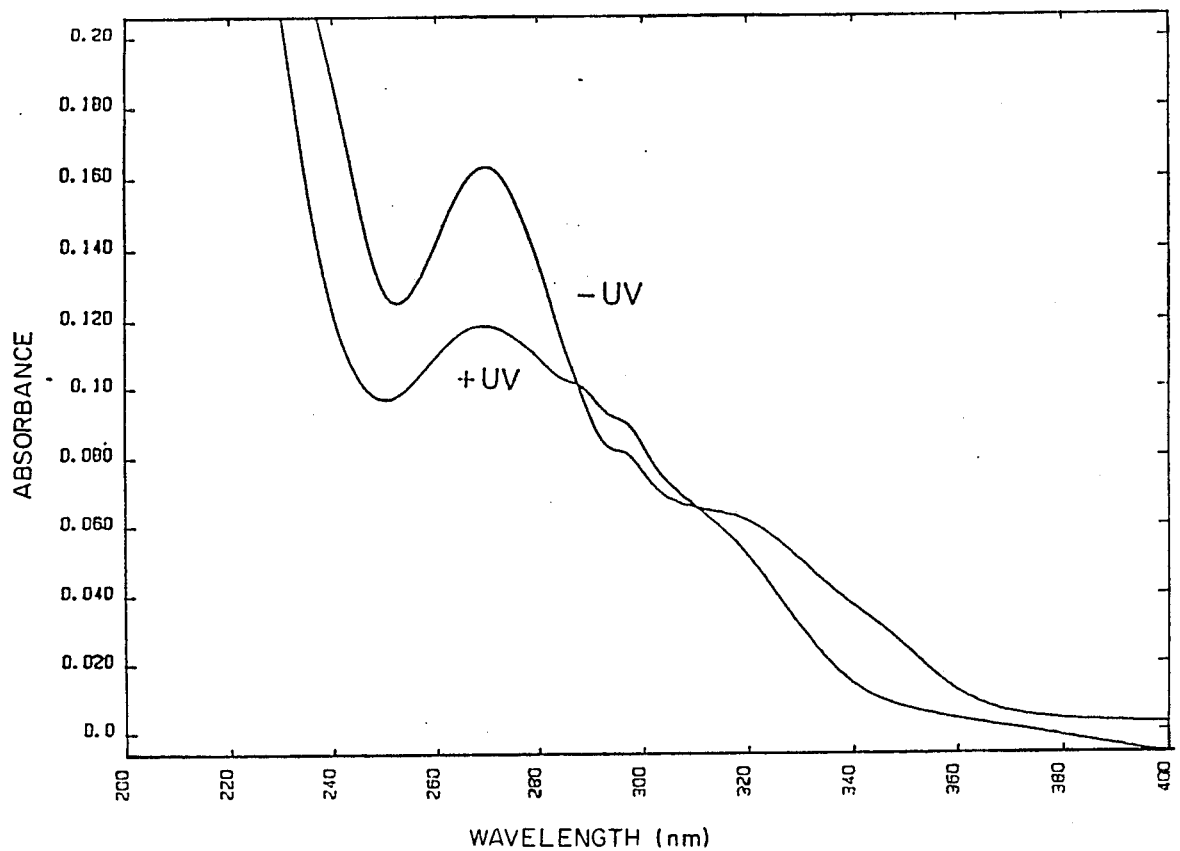
FIG. 6 shows UV-VIS absorption spectra of NASAV (−UV) and NASAV after irradiation at 302 nm for five minutes (+UV).
Figure 7:
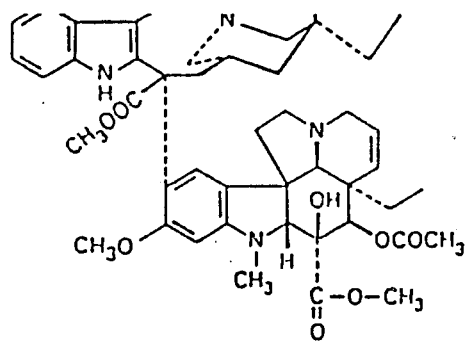
FIG. 7 shows the structures of vinblastine, N-(p-azido-[3,5-$^3$H]benzoyl)-N'-beta-aminoethylvindesine ($^3$H-NABV), and N-p-azido-[3-$^{125}$I]salicyl)-N'beta-aminoethylvindesine ($^{125}$I-NASV).
Figure 7:
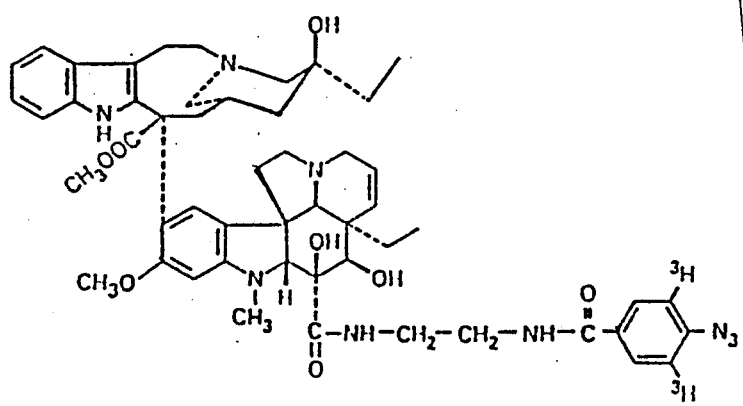
Figure 7:
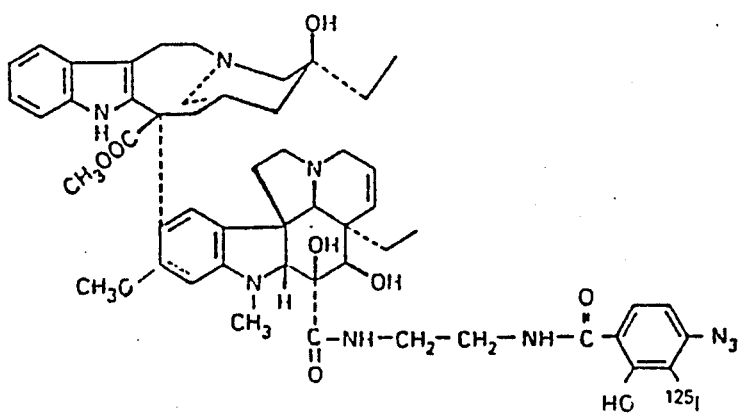
Figure 8:
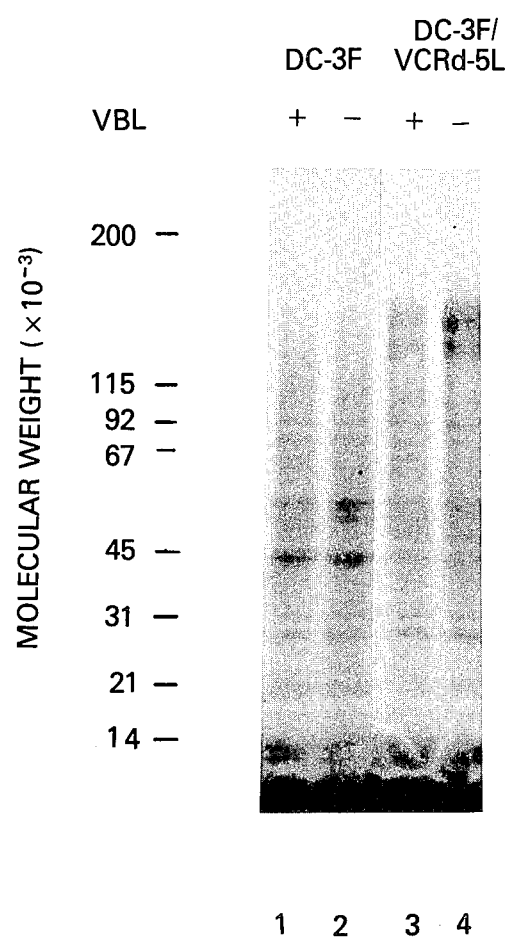

FIG. 8 shows the SDS-PAGE Fluorography of $^3$H-NABV photoaffinity labelled whole cell particulate fractions (38 micrograms of protein) of drug-sensitive Chinese hamster lung DC-3F cells (lanes 1 and 2) or drug-resistant DC-3F/VCRd-5L cells (lanes 3 and 4). Photoaffinity labelling was carried out in the presence (lanes 1 and 3) or absence (lanes 2 and 4) of 10 micromoles vinblastine. Molecular weight is expressed in daltons.

Figure 9:
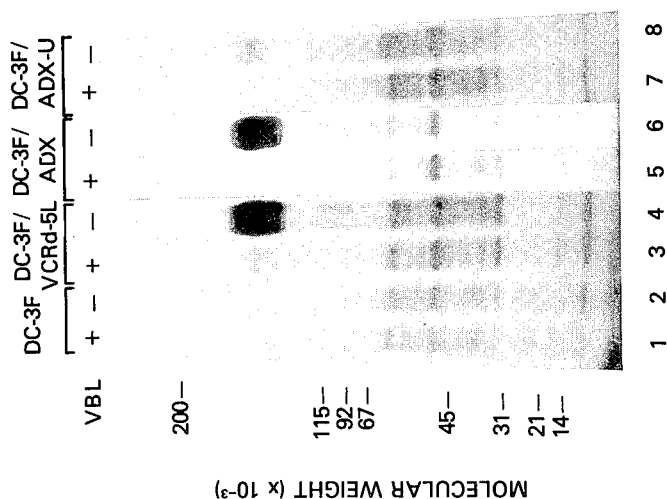

FIG. 9 shows the SDS-PAGE autoradiography of $^{125}$I-NASV photoaffinity labelled sucrose density gradient purified plasma membranes (15 micrograms protein) from drug-sensitive Chinese hamster DC-3F cells (lanes 1 and 2), drug-resistant DC-3F/VCRd-5L cells (lanes 3 and 4), drug-resistant DC-3F/ADX cells (lanes 5 and 6), and revertant DC-3F/ADX-U cells (lanes 7 and 8). Photoaffinity labelling was carried out in the presence (lanes 1, 3, 5, and 7) or absence (lanes 2, 4, 6, and 8) of 10 micromoles vinblastine. Molecular weight is expressed in daltons.

Figure 10:
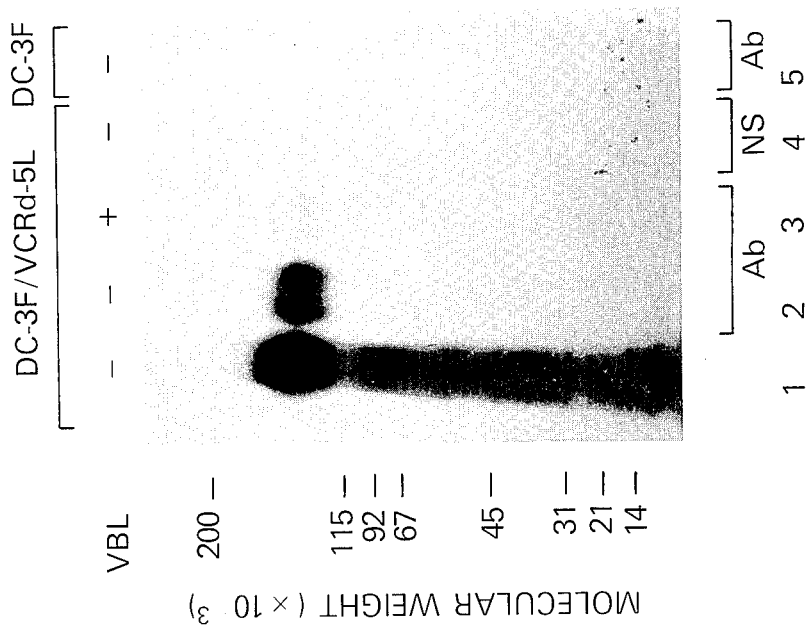

FIG. 10 shows the SDS-PAGE autoradiography of immunoprecipitates of $^{125}$I-NASV photoaffinity labelled detergent solubilized plasma membranes (20 micrograms progein) from drug-resistant DC-3F/VCRd-5L cells (lanes 1, 2, and 3) or drug-sensitive Chinese hamster DC-3F (lane 5) obtained with rabbit polyclonal antibody (ab) specific for gp150–180. Photoaffinity labelling was carried out in the presence (lane 3) or absence (lanes 1, 2, 4, and 5) of 10 micromoles vinblastine. The control was run with nonimmune rabbit serum (lane 4). A 20% recovery of gp150–180 radioactivity in the immunoprecipitate (lane 2) was indicated by comparison to the radioactivity recovered in 7.5 micrograms of photolabelled DC-3F/VCRd-5L membrane protein (lane 1). Molecular weight is expressed in daltons.

Figure 11:
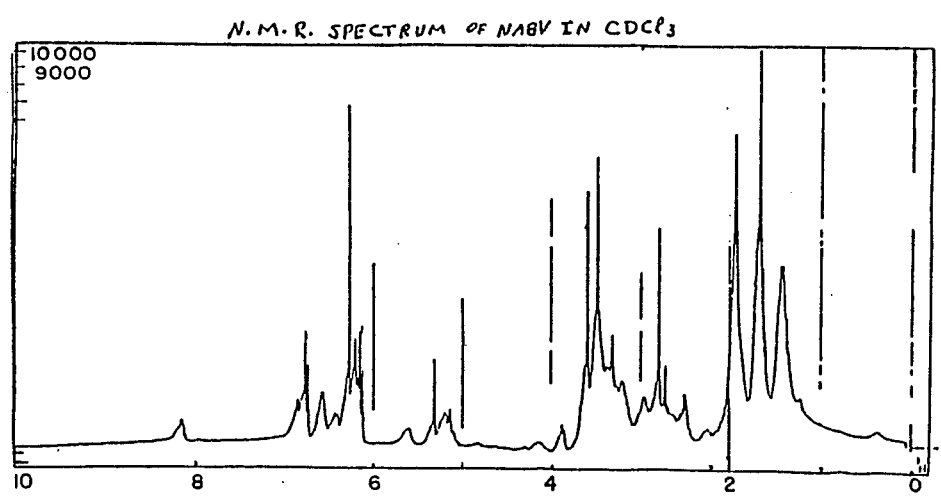

FIG. 11 shows the $^1$HNMR spectrum of NABV in $CDCl_3$ solution.

Figure 12:
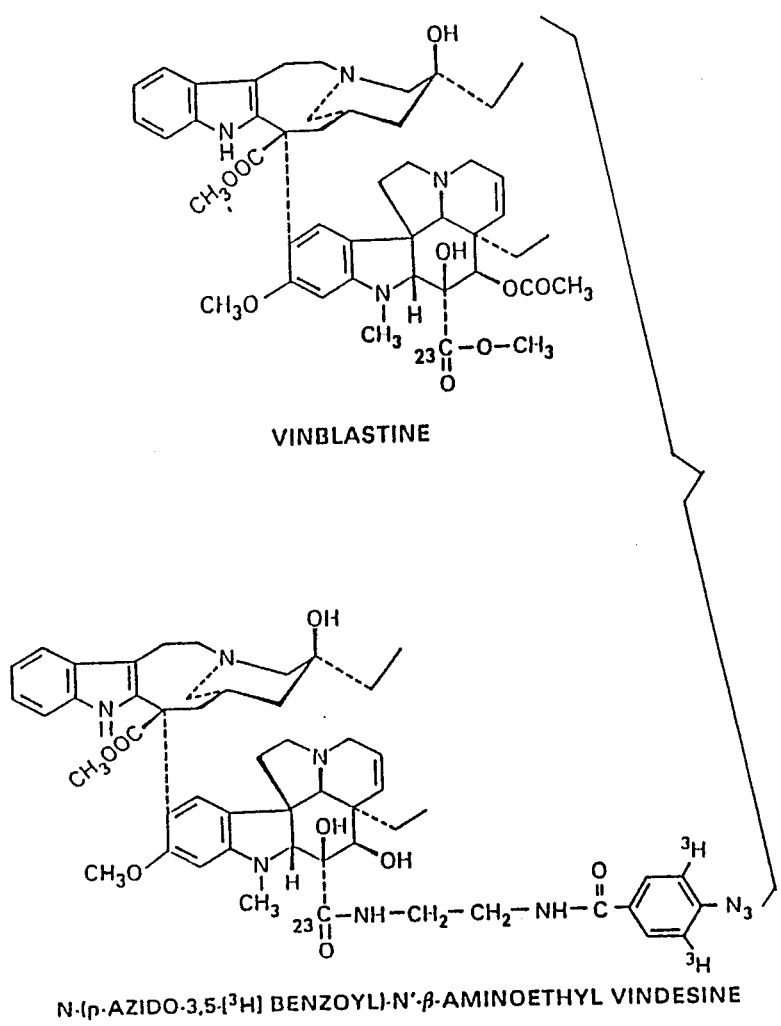

FIG. 12 shows the chemical structures of vinblastine and $^3$H-NABV.

Figure 13:
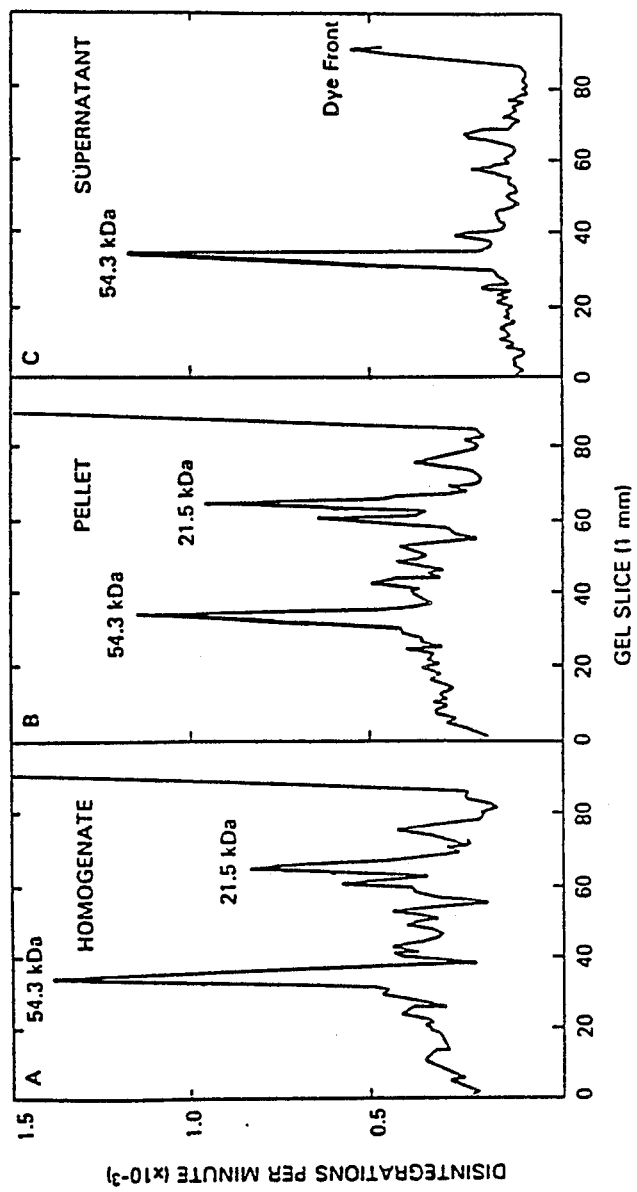

FIG. 13 shows the radioactive SDS-PAGE photolabelling profiles of (A) calf brain homogenate, (B) high speed (100,000×g, 1 h) pellet, and (c) high speed supernatant fractions. Following photoaffinity labelling of 80 micrograms protein with 50 nm (0.2 micro Ci) $^3$H-NABV and SDS-PAGE, the radioactivity in 1 mm gel slices were compated to polypeptide molecular weight standards and expressed in kilodaltons (kDa).

Figure 14:
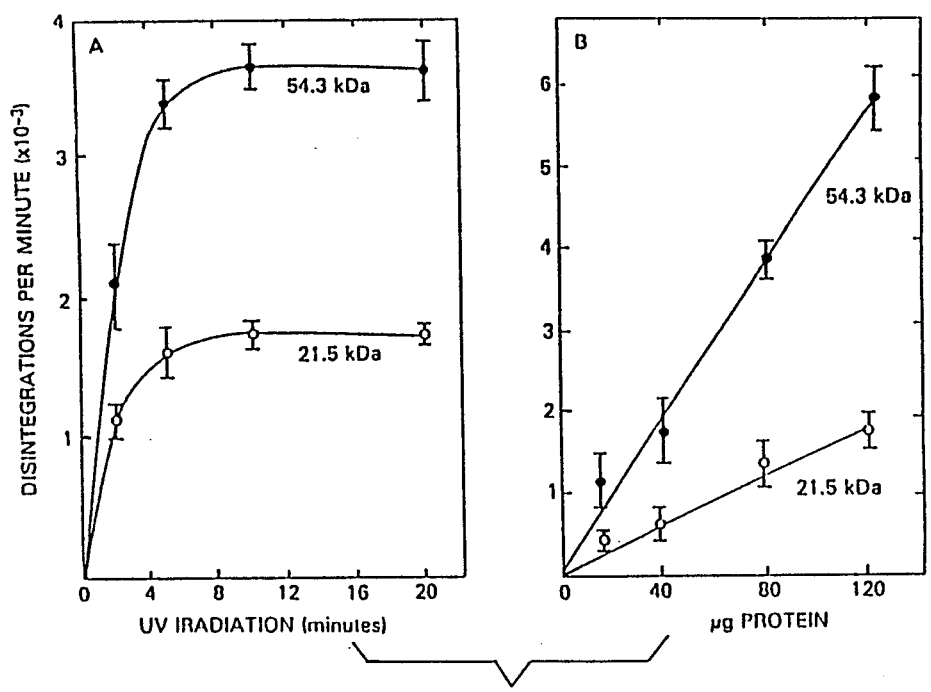

FIG. 14 shows photolabelling of claf brain homogenate (80 mg|) protein with 50 nM (0.2 microCi) $^3$H-NABV. (A) Incorporation of radioactivity into 54.3 (o) and 21.5 (o) kDa polypeptides with time of UV irradiation. (B) Incorporation of radioactivity into 54.3 (o) and 21.5 (o) kDa polypeptides as a function of calf brain homogenate protein concentration. Each point (dpm) represents the mean integrated radioactivity (n =3) minus average baseline radioactivity ± standard deviation.

Figure 15:
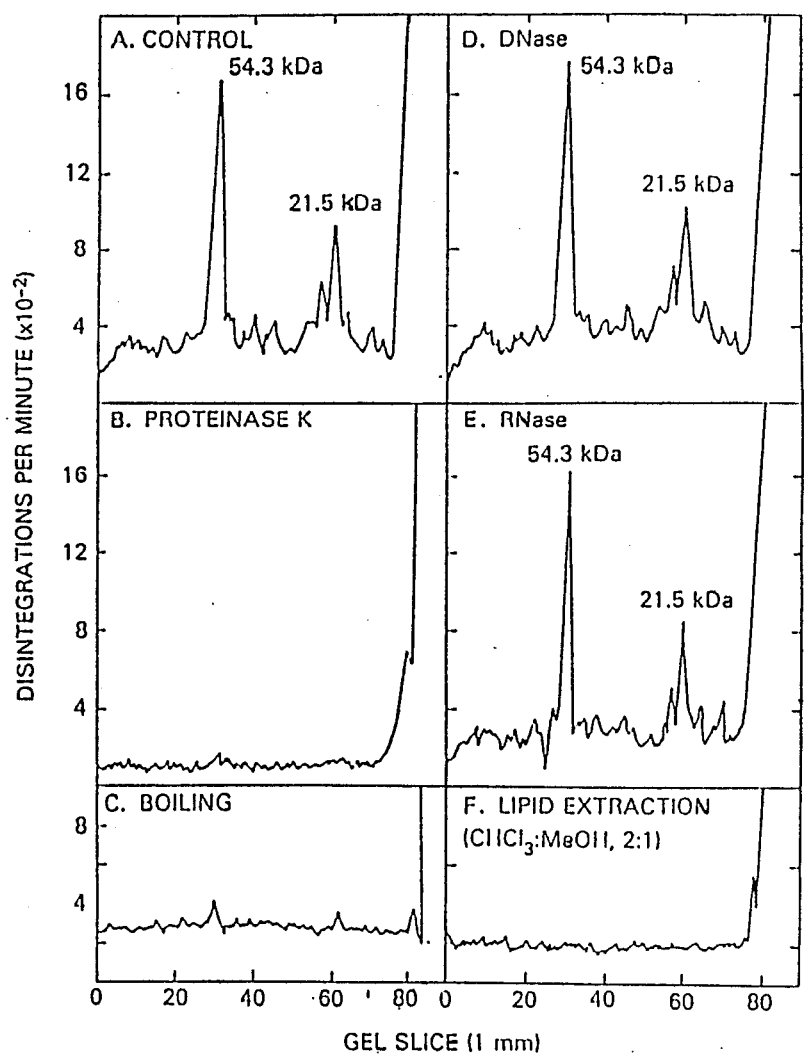

FIG. 15 shows the radioactivity SDS-PAGE profiles of calf brain homogenate following photolabelling of 80 micrograms protein with 50 nM (0.2 microCi) $^3$H-NARV, (A) untreated (control) or treated with (B0 proteinase K, (C) boiling, (D) DNase, (E) RNase, or (F) the CHCl$_3$:MeOH extraction of photolabelled calf brain homogenate.

Figure 16:
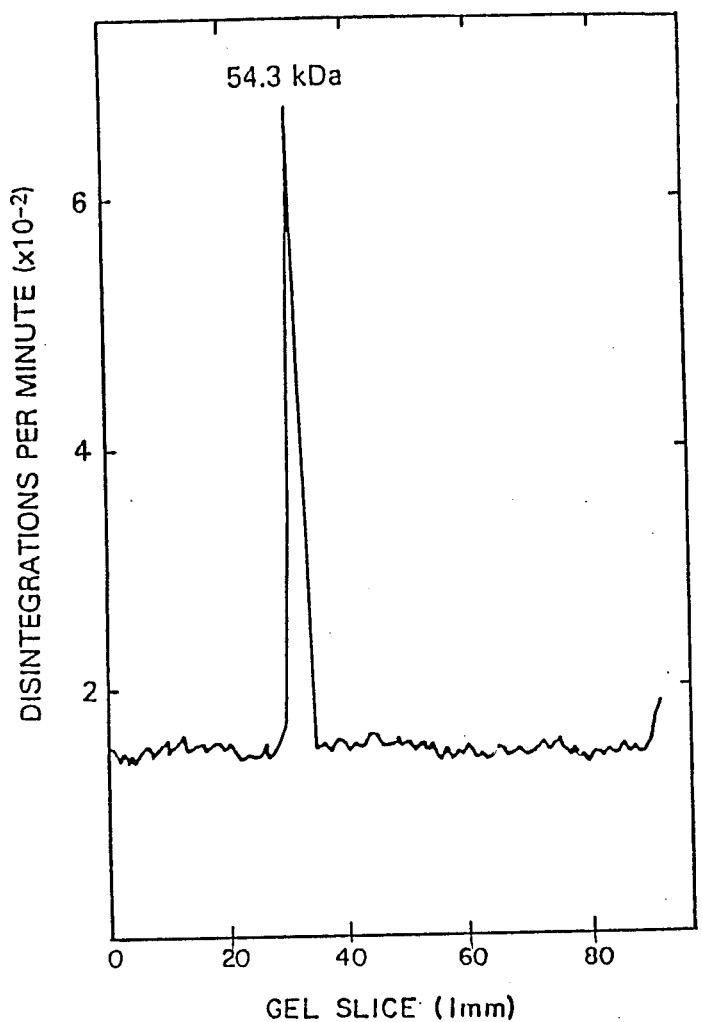

FIG. 16 shows the radioactive SDS-PAGE profile of immunoprecipitate of $^3$H-NABV photolabelled calf brain high speed supernatant fraction using monoclonal anti-alpha-tubulin.

Figure 17:
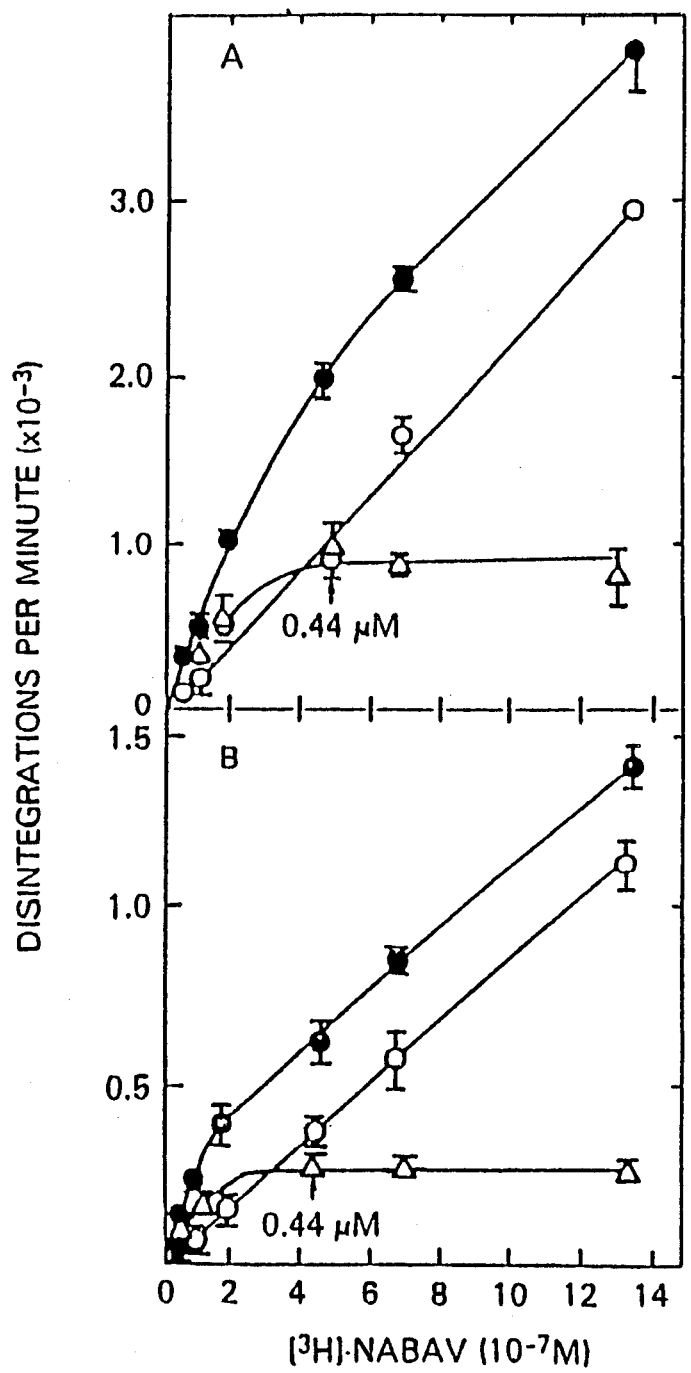

FIG. 17 shows photolabelling of the 54.3 (A) and 21.5 (B) kDa polypeptides in 65 micrograms calf brain homogenate protein with increasing $^3$H-NABV concentrations (2.02 Ci/mmol). The homogenate protein and different concentrations of $^3$H-NABV with and without 20 micromoles vinblastine were photolabelled for 15 minutes. The subtraction of radioactivity incorporated in the presence (·) from the radioactivity incorporated in the absence (o) of vinblastine represents the net specific photolabelling (Δ). Each point represents the mean integrated radioactivity (n=3) minus average baseline radioactivity ± standard deviations.

Figure 18:
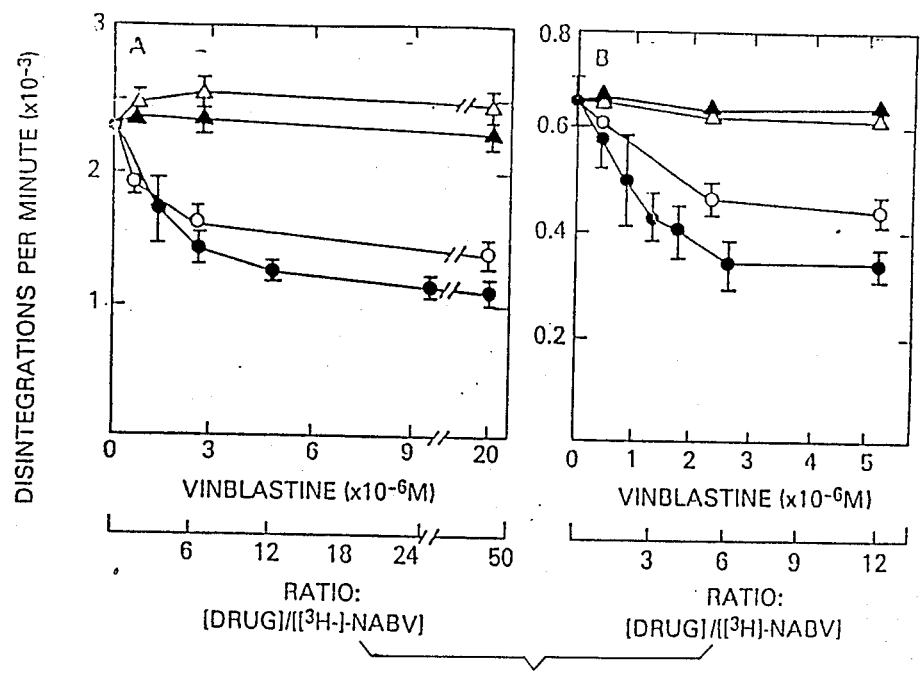

FIG. 18 shows photoaffinity labelling of the (A) 54.3 and (B) 21.5 kDa polypeptides in calf brain homogenate (65 micrograms protein) with 0.44 micromoles $^3$H-NABV (2.02 Ci/mmole) in the presence of increasing concentrations (1-22 micromoles) of vinblastine (·), vincristine (o), colchicine (Δ) and daunorubicine (Δ). Each point represents the mean integrated radioactivity (n=3) minus average baseline radioactivity ± standard deviation.

Figure 19:
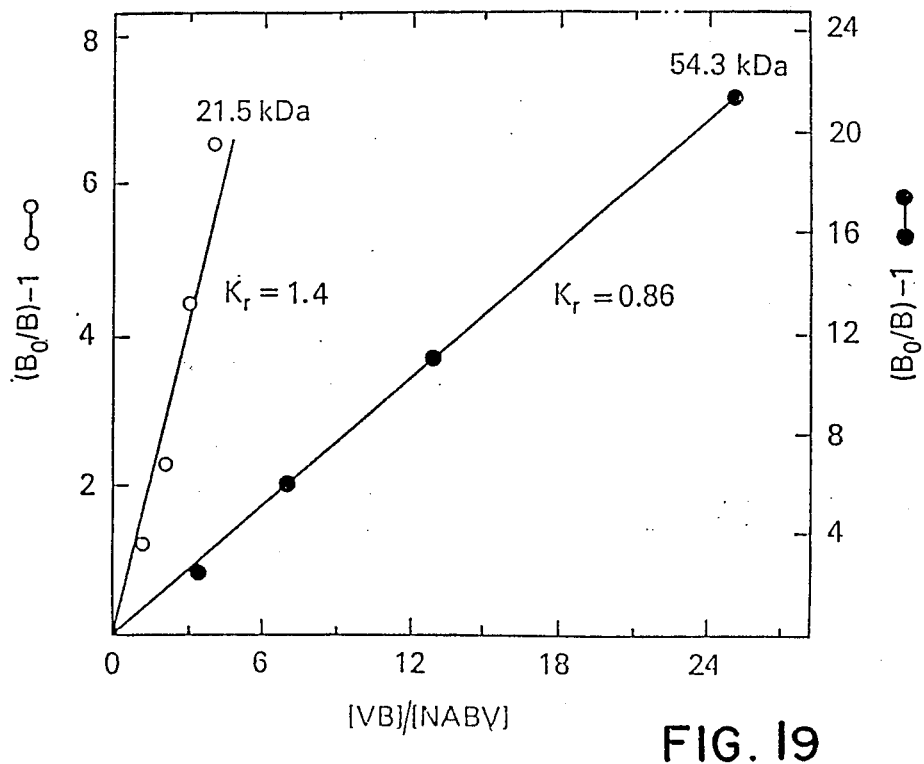

FIG. 19 is a replot of the competitive binding data from FIG. 18. The relative association constants (K$_r$) of vinblastine to that of NABV for 54.3 (o) and 21.5 kDa (o) polypeptides were estimated from the equation (Bo/B)-1 =K$_r$[VB]/[NABV](32.33) where Bo and B are radioactive incorporation in the absence and presence of vinblastine, respectively.

Synthesis and Characterization of N-(p-azidobenzoyl)-N'-beta-aminoethylvindesine The photoactive Vinca alkaloid analog, NABV, was prepared from vinblastine by N-azidobenzoylation of N-beta-aminoethylvindesine with N-hydroxysuccinimidyl-4-azidobenzoate. The analog was purified with high pressure liquid chromatography. Values of the absorption peaks measured by infrared, the response frequencies measured by HNMR and the FAB mass spectral analysis confirmed the structure of NABV. The UV-VIS absorption spectrum of the product showed a closed composite of the absorption spectra of its p-azidobenzoyl chromophore, and the absorption spectra of vinblastine between 180-340 nm. Irradiation with UV light caused a time-dependent loss in 250-300 nm absorption of NABV yielding a final spectrum very similar to vinblastine. The UV-spectrum of the parent compound, vinblastine, was not affected by UV light.

Under standard photolabelling conditions used, no appreciable metabolism of the photoactive Vinca alkaloid analog was detected. This was confirmed by incubating $^3$H-NABV with brain homogenates in the dark for 30-60 minutes at 0°, 25°, and 37° C., subsequently extracting the mixtures with chloroform, and analyzing for radioactive metabolites by silica gel thin layer chromatography and high pressure liquid chromatography. A single radioactive spot corresponded to the R$_f$ of NABV and accounted for more than 98% of the recovered radioactivity.

Photolabelling of Calf Brain Vinca Alkaloid Acceptors

Photolabelling profiles were obtained by UV irradiation of mixtures of $^3$H-NABV and calf brain homogenate, high speed pellet or supernatant fractions, followed by SDS-PAGE and comparison of the radioactivity in 1 mm gel slices relative to the migration of polypeptide molecular weight standards. Photolabelling of brain homogenate revealed a number of distinct labelled components superimposed on a baseline of nonspecific radioactivity (2-4 times ambient background) distributed throughout the gel. The most prominently labelled species (54.3 kDa) was found in both the high speed supernatant and pellet fractions. Another prominently labelled component (21.5 kDa) was found only in the high speed pellet. Additionally, a number of other components were photolabelled weakly (i.e., 14, 26, and 44 kDa species). Maximum photolabelling of the 54.3 and 21.5 kDa components was observed after 10-12 minutes of UV irradiation. Total incorporation of $^3$H-NABV into the 54.3 and 21.5 kDa polypeptides increased linearly with protein concentration up to 120 micrograms protein. When the photolabelling profiles were compared to densitometry tracings of Coomassie brilliant blue stained brain homogenate after SDS-PAGE, it was found that the 54.3 and 21.5 kDa components incorporated 8-10 times the radioactivity per coincident stained polypeptide as for the average background labelling. Identical radioactivity profiles were obtained after preincubation of $^3$H-NABV with calf brain homogenates for 1, 30, or 60 minutes followed by photolabelling at 25° or 37° C. for 10 minutes.

When homogenate was incubated with $^3$H-NABV in the absence of UV light for 30 minutes, no radioactivity was found in subsequent SDS-PAGE gel slices above the ambient background level, except for excess 3H-NABV which migrated near the tracking dye front. Similar results were obtained after photoactivating $^3$H-NABV in the absence of brain homogenate which was then added prior to performing SDS-PAGE and gel slice analysis. Moreover, under standard photolabelling conditions, no radiolabel incorporation into calf brain macromolecular components was detected using $^3$H-vinblastine.

Characterization of Photolabelled Components

The protein nature of photolabelled components was established with specific hydrolytic enzymes. Proteinase K treatment of photolabelled brain homogenates totally abolished all the major labelled components as well as the nonspecific baseline radioactivity, confirming the polypeptide composition of the photolabelled components. When the homogenates were boiled for 20 minutes and quickly cooled prior to photolabelling, the radioactive incorporation of the 54.3 and 21.5 kDa polypeptides was reduced greater than 80%, while nonspecific radioactive incorporation throughout the gel was unchanged. This finding was consistent with a specific protein conformation-dependent recognition of NABV beyond that which would be expected from random low affinity interactions with native or denatured proteins. Furthermore, treatment with DNase or RNase had no effect on either specific or nonspecific photolabelling. In addition, no radioactive macromolecular components were found in the organic layer following extraction of the photolabelled brain homogenates with chloroform:methanol (2:1).

Identification of 54.3 kDa Polypeptide

The photolabelled 54.3 kDa polypeptide in the high speed supernatant fraction or in detergent solubilized high speed pellet fraction was identified as a tubulin subunit by immunoprecipitation with monoclonal antibody to alpha- or beta-tubulin antibody. When the resultant immunoprecipitates of high speed supernatant or pellet fractions were analyzed by SDS-PAGE, 40–45% of the photolabelled 54.3 kDa polypeptide was recovered in the immunoprecipitant as a 54.3 kDa polypeptide.

Vinca Alkaloid Specificity of Photolabelled Polypeptides

Photolabelling specificity was analyzed by labelling brain homogenates with increasing concentrations of $^3$H-NABV (0–1.32 micromoles) in both the absence and presence of excess vinblastine. In the absence of vinblastine, the 54.3 and 21.5 kDa polypeptides exhibited a biphasic increase in radiolabelling which is characteristic of mixed specific and nonspecific photolabelling. In the presence of excess vinblastine, specific Vinca alkaloid photolabelling was blocked and the incorporation of radioactivity into both polypeptides increased linearly with a slope parallel to the terminal nonspecific linear portion of the biphasic curves. The specific photolabelling was obtained by subtracting the nonspecific linear curve from the mixed biphasic profile. After correcting for nonspecific labelling, the 54.3 and 21.5 kDa polypeptides exhibited half maximal saturation photolabelling at 2.08 and $0.95\times10-7$M $^3$H-NABV with maximum saturable incorporation of 5.5 and 0.9 pmol $^3$H-NABV bound/mg of calf brain homogenate protein, respectively.

At a fixed saturating $^3$H-NABV concentration (0.44 micromoles), increasing concentrations of vinblastine gradually reduced the specific labelling to a limiting minimum of about 50% of the total photolabelling in the absence of competitor. The portion of radioactive labelling not blocked corresponds to nonspecific incorporation and agress closely with the percent of total labelling ascribed to nonspecific labelling (48% and 51%, respectively) in the saturation photolabelling experiments. In order to estimate the relative association constant of vinblastine to that of NABV (Kr), the competition data from FIGS. 9A and 9B were analyzed as originally suggested by Ofenggand et al *J. Biol. Chem.* 2446241-6253 (1969) in photolabelling experiments. The linear replot indicates that the effect of vinblastine on the binding of $^3$H-NABV is by simple competition. More importantly, the slopes of these replots $K_r$=Ka vinblastine/Ka NABV (Ka=association constant), of 0.86 and 1.4 for the 54.3 and 21.5 kDa polypeptides, respectively, indicate that the binding of NABV and vinblastine to both the respective polypeptides was similar. Also, while increasing concentrations of vincristine significantly decreased photolabelling of the 54.3 and 21.5 kDa polypeptides, daunorubicin and colchicine has negligible effects. In the presence of 20 micromoles of vinblastine, photolabelling of the 14, 26, and 44 kDa polypeptides was decreased approximately 40% while the overall nonspecific radiolabelling was unaffected.

Effect of a Nitrene Scavenger on Photolabelling of Vinca Alkaloid Binding Polypeptides The photolablelling of brain homogenate in the presence of the nitrene scavenger, p-aminobenzoic acid, in 100-fold excess ofer [$^3$H]-NABV caused a small but statistically significant reduction (25%) of photolabelling of the 54.3 kDa polypeptide. However, no significant further reduction was observed up to $10^4$-fold molar excess. In contrast, although a $10^3$-fold molar excess of scavenger had no significant effect on photolabelling of the 21.5 kDa polypeptide, a 30% reduction was observed at $10^4$-fold molar excess of scavenger.

As can be clearly seen from the above examples, NABV is a photoactive Vinca alkaloid analog which retains the biological and pharmacological properties of vinblastine. The analog can be used to identify specific cellular components which interact with Vinca alkaloids and may have a significant relationship to the pronounced antimitotic, cytotoxic, and antineoplastic activities of this class of drugs. Since the biological activity of the Vinca alkaloids has been found to reside primarily in the cathatanthine moiety (the upper indole moiety of the dimeric alkaloid), the chemical changes leading to the synthesis of NABV were carried out by modification of the $C_{23}$-ester of the vindoline moiety (the lower indole moiety) of vinblastine.

Further studies have shown that NABV retained the pharmacological and biological activities of vinblastine. After 72 hours exposure, the IC50 values of exponentially growing P388 murine leukemic cells were 1.1 nM for NABV and 0.6 nM for vinblastine. Ultrastructural alterations induced by NABV in P388 leukemic cells and MCF-7 human breast tumor cells, such as the formation of microtubular paractystals, mitotic arrest, and the appearance of multinucleated cells, resembles those caused by vinblastine. Also, both drugs inhibit in vitro microtubule assembly, induce tubulin aggregation, and inhibit tubulin-dependent GTP hydrolysis at similar concentrations. Thus, NABV is ideal for probing intracellular Vinca alkaloid interactions because it retains the known biochemical and pharmacological properties of this class of drugs.

Specific Vinca alkaloid binding macromolecules were identified in calf brain by photoaffinity labelling with $^3$H-NABV. Photolabelling predominantly labelled polypeptides of 54.3 and 21.5 kDa in brain homogenates, although a number of other polypeptides appeared to be labelled specifically, although weakly. The results obtained are consistent with a specific high affinity recognition of the photoactive analog by the 54.3 and 21.5 kDa polypeptides, as shown by the following evidence:

(1) both exhibited saturable photolabelling characteristic of formation of specific reversible binary complexes between NABV and polypeptide acceptors;

(2) saturable photolabelling was readily blocked by vinblastine or vincristine, but not by colchicine and daunorubicin;

(3) although it was not possible to determine true equilibrium constants from the saturable photolabelling, the half maximum saturation of 54.3 kDa photolabelling with respect to concentration of $^3$H-NABV is similar to reported dissociation constants of tubulin for vinblastine; by analogy, since the half maximum saturation value of the photolabelled 21.5 kDa polypeptide is even lower than that of 54.3 kDa, it can be concluded that the 54.3 and 21.5 kDa polypeptides have similar affinities for vinblastine;

(4) the ratios of association constants of vinblastine and NABV for the 54.3 and 21.5 kDa polypeptides near unity indicate that the vinblasitne and its photoactive analog have similar affinity for vinblastine binding sites. In addition, only a modest effect on the photolabelling of the 54.3 and 21.5 kDa polypeptides by an excess of the nitrene scavenger, p-aminobenzoic acid, was consistent with the majority of the total photolabelling resulting at specific affinity binding sites.

The 54.3 kDa component was the most heavily labelled polypeptide, and was found in both the high speed supernatant and the particulate membrane fractions. The membrane-associated 54.3 kDa polypeptide was not liberated by repeated washing with moderate salt concentrations, but was solubilized with detergent, suggesting that it is an integral membrane associated component. Both the supernatant fraction and the detergent membrane solubilized 54.3 kDa polypeptide were identified as a tubulin subunit on the basis of coelectrophoresis with purified calf brain tubulin by SDA-PAGE, subcelluar distribution, and immunoprecipitation with anti-tubulin subunit monoclonal antibodies.

The function of membrane tubulin is not known; it is possible that it plays a role in a number of membrane related phenomena associated with the physiological and cytotoxic effects of the Vinca alkaloids. Although it has been suggested that the interaction of Vinca alkaloids with tubulin of the microtubules is the mods by which cytotoxicity and the characteristic peripheral neuropathy are expressed, the molecular basis for these events remains unexplained. The presence of tubulin in the membrane fraction also would account for the suggestion that there is a role for the intact cytoskeleton in both membrane mobile or cytoplasmic mobile transfer steps involving receptor molecules. It is known that the Vinca alkaloid induce changes in plasma membrane transport, as well as magnify the induction of cAMP by beta-adrenergic hormones, prostaglandin E, and isoproterenol. This last effect indicates the influence of these drugs on adenylate cyclase or phosphodiesterase, even though the Vinca alkaloids lack intrinsic phosphodiesterase inhibitory activity.

The identification of a specific membrane Vinca alkaloid binding 21.5 kDa polypeptide provides another component that could play a central role in mediating the effect of these drugs. The nontubulin nature of this protein was demonstrated when immunoblotting of the detergent solubilized calf brain membrane fraction with anti-tubulin monoclonal antibodies detected only tubulin. Other Vinca alkaloid binding polypeptides which are weakly photolabelled may also play a unique role in initiating or mediating the effects of these drugs.

It can be seen from the above that NABV is an important probe for identifying the cellular components which may initiate or mediate the known as well as novel biochemical mechanisms of Vinca alkaloid action.

The foregoing description of the specific embodiment(s) will so fully reveal the general nature of the invention that others can, by applying current knowledge, readily modify and/or adapt for various applications such specific embodiment(s) without departing from the generic concept, and, therefore, such adaptations and modifications should and are intended to be comprehended within the meaning and range of equivalents of the disclosed embodiment(s). It is to be understood that the phraseology or terminology employed herein is for the purpose of description and not of limitation.

What is claimed is:

1. N-(p-azido-[3,4-$^3$H]benzoyl)-N'-beta-aminoethylvindesine.

2. N-(p-azidosalicyl)-N'-beta-aminoethylvindesine.

3. N-(p-azidobenzoyl)-N'-beta-aminoethylvindesine.

4. A reagent composition for photolabelling cells for determining the affinity of the cells for vinblastine comprising N-(p-azido-[3,4,$^3$H]-benzoyl)-N'beta-aminoethylvindesine and a suitable carrier.

5. A reagent composition for radiolabelling cells to determine the affinity of the cells for vinblastine comprising N-(p-azido-3-[$^{125}$I]-salicyl-N'-beta-aminoethylvindesine and a suitable carrier.

* * * * *